US012667474B2

(12) United States Patent
Mehndiratta et al.

(10) Patent No.: US 12,667,474 B2
(45) Date of Patent: Jun. 30, 2026

(54) SYSTEM FOR REHABILITATION OF A LIMB OF A PATIENT

(71) Applicant: INDIAN INSTITUTE OF TECHNOLOGY DELHI, New Delhi (IN)

(72) Inventors: Amit Mehndiratta, New Delhi (IN); Neha Singh, New Delhi (IN)

(73) Assignee: INDIAN INSTITUTE OF TECHNOLOGY DELH, New Delhi (IN)

( * ) Notice: Subject to any disclaimer, the term of this patent is extended or adjusted under 35 U.S.C. 154(b) by 1209 days.

(21) Appl. No.: 17/625,958

(22) PCT Filed: Jul. 10, 2020

(86) PCT No.: PCT/IN2020/050600
§ 371 (c)(1),
(2) Date: Jan. 10, 2022

(87) PCT Pub. No.: WO2021/005626
PCT Pub. Date: Jan. 14, 2021

(65) Prior Publication Data
US 2022/0249266 A1 Aug. 11, 2022

(30) Foreign Application Priority Data
Jul. 10, 2019 (IN) .............................. 201911027688

(51) Int. Cl.
*A61F 4/00* (2006.01)
*A61F 2/72* (2006.01)
*A61N 1/36* (2006.01)

(52) U.S. Cl.
CPC .................. *A61F 4/00* (2013.01); *A61F 2/72* (2013.01); *A61N 1/36003* (2013.01); *A61N 1/36103* (2013.01)

(58) Field of Classification Search
CPC ...... A61F 2/68; A61F 2/72; A61F 2002/6827; A61F 2005/0155; B25J 9/0006
(Continued)

(56) References Cited

U.S. PATENT DOCUMENTS

| | | | |
|---|---|---|---|
| 8,121,694 B2 * | 2/2012 | Molnar | A61B 5/4082 607/45 |
| 2006/0206167 A1 * | 9/2006 | Flaherty | A61H 3/008 607/48 |

(Continued)

FOREIGN PATENT DOCUMENTS

| | | |
|---|---|---|
| EP | 2166935 B1 | 10/2018 |
| WO | 2017120484 A1 | 7/2017 |
| WO | 2019028394 A1 | 2/2019 |

*Primary Examiner* — Brandy S Lee
*Assistant Examiner* — Mishal Zahra Hussain
(74) *Attorney, Agent, or Firm* — Dickinson Wright PLLC

(57) ABSTRACT

The invention relates to a system (100), for rehabilitation of a limb of a patient, that comprises a controller (110) communicatively coupled to an activity monitor (102) and operatively coupled to a robotic exoskeleton unit (104) and a brain stimulation unit (106). The activity monitor (102) detects an activity of the limb of the patient by a voluntary attempt of the patient in a first time frame and communicates the voluntary attempt to the controller over a second time frame. The robotic exoskeleton unit completes the movement of the limb, and the brain stimulation unit externally stimulates a local motor region of a brain of the patient based on the effort signal reaching a pre-specified threshold to complete a sensorimotor loop.

9 Claims, 3 Drawing Sheets

(58) Field of Classification Search
USPC ........................................................... 623/27
See application file for complete search history.

(56) References Cited

U.S. PATENT DOCUMENTS

| | | | |
|---|---|---|---|
| 2008/0045775 A1* | 2/2008 | Lozano | A61N 1/36082 |
| | | | 600/12 |
| 2015/0012111 A1* | 1/2015 | Contreras-Vidal | A61B 5/369 |
| | | | 623/25 |
| 2017/0042713 A1* | 2/2017 | Nurmikko | A61B 5/1113 |
| 2019/0021883 A1* | 1/2019 | Herr | A61F 2/64 |
| 2019/0038438 A1* | 2/2019 | John | A61B 5/4851 |
| 2020/0363869 A1* | 11/2020 | Yoo | A61B 5/24 |

* cited by examiner

SYSTEM FOR REHABILITATION OF A LIMB OF A PATIENT

FIELD OF INVENTION

The present subject matter relates, in general, to rehabilitation of disabled limbs, in particular, to bio-engineered rehabilitation of upper and lower limbs, disabled due to stroke, brain injury, spinal cord injury and neuromuscular disorders like, cerebral palsy, multiple sclerosis etc.

BACKGROUND

In general, bio-engineered rehabilitation is performed by non-invasive brain stimulation therapy that can be either electrical or magnetic stimulation. The therapy is performed on primary motor cortex or premotor cortex or dorsolateral prefrontal cortex, which improves the upper limb functions.

BRIEF DESCRIPTION OF DRAWINGS

The detailed descriptions are depicted with reference to the accompanying figures. In the figures, the left-most digit(s) of a reference number identifies the figure in which the reference number first appears. The same numbers are used throughout the figures to reference like features and components. Some implementations of the system(s), in accordance with the present subject matter, are described by way of examples, and with reference to the accompanying figures, in which.

DETAILED DESCRIPTION

Figure 1:
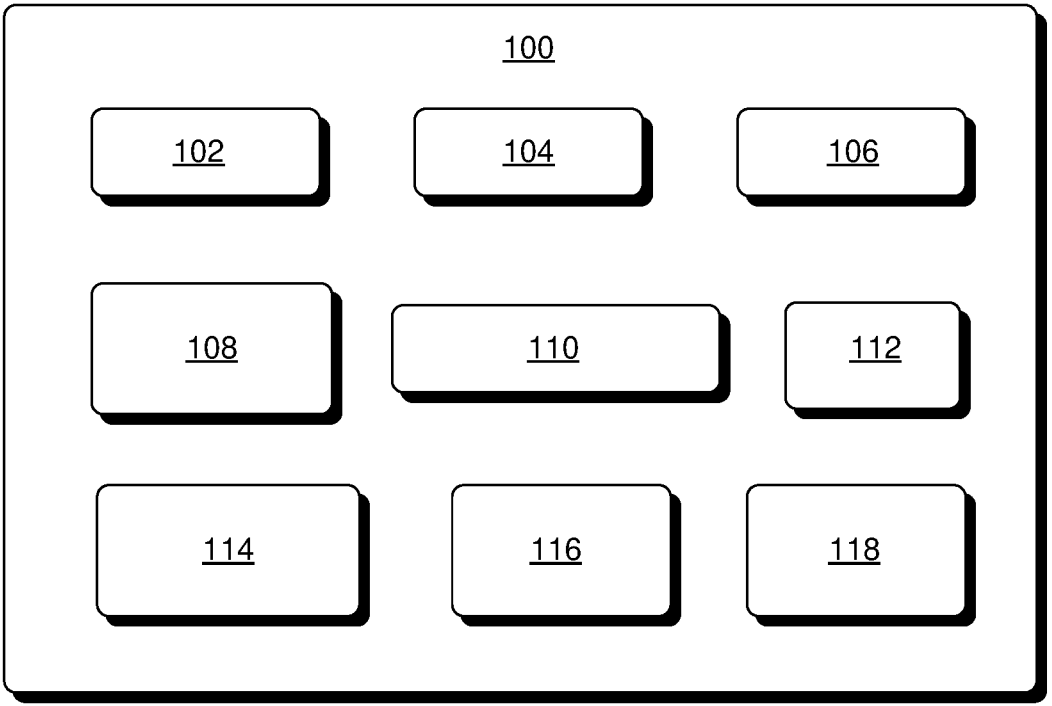
FIG. 1 illustrates a block diagram of a system for rehabilitation of a limb of a patient, in accordance with an example implementation of the present subject matter.

Rehabilitation is a clinically accepted treatment that restores a functional ability of patients with physical impairments or disabilities. The rehabilitation is a long-term process. Non-invasive brain stimulation is an effective technique to alter the neural activities of the brain. A magnetic field is created around the head that generates magnetic pulses to stimulate the brain by inducing low-intensity current inside the brain through the scalp.

In conventional non-invasive brain stimulation systems, high frequency stimulation on ipsilesion hemisphere or low frequency magnetic stimulation on contralesion-hemisphere enables improvement in the upper limb functions. The modulatory effects generated due to high frequency or low frequency magnetic stimulation are non-focused and non-specific. In conventional non-invasive brain stimulation systems, the stimulation is performed in a pre-defined manner, irrespective of the brain state of the patient and without direct involvement of the patient, therefore depending on the brain state is not possible. The conventional non-focused and non-specific stimulation of the brain, is performed on Abductor Pollicis Brevis (APB)/Flexor Pollicis Brevis (FPB) muscle. The conventional non-focused and non-specific stimulation of the brain is not effective in rehabilitating a specific impaired muscle or a limb associated with a specific impaired portion of the brain. The ineffectiveness in the rehabilitation may be caused as stimulation on a specific impaired portion of the brain, which is related to a specific disabled limb, is not performed. Also, the patient just lies on chair with the brain stimulation with pre-defined low/high frequency being done with no direct involvement of the patient. Hence, the brain stimulation is passive brain stimulation.

To this end, a system for rehabilitation of a limb of a patient is proposed, which enables direct involvement of the patient, making the brain stimulation active (during patient voluntary activity) brain stimulation, and also providing the stimulation of a specific paretic muscle representation in brain (of impaired muscle) of the patient.

In one implementation of the present subject matter, the system includes an activity monitor that detects an activity of a limb of a patient within a first pre-specified time frame by a voluntary attempt of the patient. In an example, the first pre-specified time frame is 3 seconds. As per the patient specific condition/symptoms, the patient feeds the parameters (according to the individual patient clinical symptoms), detected by a controller, at the very start of the interventional therapy for each patient. Upon the expiry of the first prescribed time frame, an effort signal is processed over a second pre-specified time frame. The effort signal is a feedback of how much was the voluntary attempt (performance feedback) to the patient. In an example, the second pre-specified time frame is 7 seconds. Once the activity in the first pre-specified time is detected by the activity monitor, the activity monitor detects the activity and sends command to the controller at the start of second pre-specified time, to enable a robotic exoskeleton unit to assist the movement of the limb of the patient by performing the movement in the second pre-specified time corresponding to an effort signal generated by the activity of the limb of the patient and detected by a controller. The incomplete movement of the limb of the patient is completed by the assistance of the robotic exoskeleton unit, in the second pre-specified time. A brain stimulation unit stimulates a local motor region of a brain of the patient simultaneously with the robotic exoskeleton unit, at the start of the second pre-specified time. The external stimulation of the brain by the local motor region of a brain of the patient and robotic exoskeleton unit assisting the movement completes a sensorimotor loop.

Therefore, the limb of the patient is rehabilitated based on the guidance provided by the physiological signals of the patient, in which an (patient) activity dependent stimulation of the brain is performed. The activity dependent brain stimulation enables the stimulation of a specific paretic muscle of the patient when attempting a particular movement (activity). The activity dependent stimulation provides strength to the synapses responsible for the movement of the muscle required for a particular movement while the movement is being assisted by the exoskeleton unit.

In the activity dependent brain stimulation by the brain stimulation unit, direct participation of the patient improves the therapeutic effect as the patient is encouraged to voluntarily take part in the therapy, which leads to voluntary depolarization of the pyramidal neurons of the cortex and therefore, even only a single pulse of brain stimulation (as for example via Transcranial Direct Current Stimulation (TDCS) or Transcranial magnetic stimulation: TMS) might be sufficient to depolarize the neurons. The activity dependent brain stimulation synchronizes the brain stimulation with neural activity and facilitates Hebbian plasticity that claims that synaptic efficacy increases from a presynaptic cell's repeated and persistent stimulation of a postsynaptic cell.

The actions of primary motor cortex are improved by practicing the movements associated with the primary motor cortex and the brain stimulation during motor training on the primary motor cortex modulates the primary motor cortex and its connections leading to more functionally appropriate use dependent plasticity and improved ability of the brain to change or form new connections between brain cells. Motor training promotes use-dependent plasticity because Long Term Potentiation effects preferentially target specific functional areas through Hebbian mechanism. Thus, brain stimulation and motor training together are likely to be synergistic in promoting functional neuroplastic changes that brain stimulation last well beyond the period of therapy. Thus, a faster recovery related to neuromuscular disorders of the patients is enabled.

These and other advantages of the present subject matter would be described in a greater detail in conjunction with FIGS. 1-3 in the following description. The manner, in which the limb of the patient is rehabilitated and used shall be explained in detail with respect to FIGS. 1-3. It should be noted that the description merely illustrates the principles of the present subject matter. It will thus be appreciated that those skilled in the art will be able to devise various arrangements that, although not explicitly described herein, embody the principles of the present subject matter and are included within its scope. Furthermore, all examples recited herein are intended only to aid the reader in understanding the principles of the present subject matter. Moreover, all statements herein reciting principles, aspects and implementations of the present subject matter, as well as specific examples thereof, are intended to encompass equivalents thereof.

FIG. 1 illustrates a block diagram of a system 100 for rehabilitation of a limb of a patient, in accordance with an example implementation of the present subject matter. The system 100 for rehabilitation of a limb of a patient, herein may be referred to as a system 100. The system 100 may be implemented as a computer, for example a desktop computer, a laptop, server, and the like. In one example, the system 100 is a hardware unit. The system 100 includes an activity monitor 102, a robotic exoskeleton unit 104, a brain stimulation unit 106, a memory 108, a controller 110, a processing module 112, data 114, a user interface 116 and a feedback unit 118.

The controller 110 may be coupled to the user interface 116 for setting the parameters, such as amount of physiological signals patient can generate, speed and range of movement of the limb of the patient to be executed by the robotic exoskeleton unit 104. The controller 110 may be implemented through a combination of any suitable hardware and computer-readable instructions. The controller 110 may be implemented in a number of different ways to perform various functions for the purposes of operating the activity monitor 102, the robotic exoskeleton unit 104, the feedback unit 118 and the brain stimulation unit 106, in accordance with example implementations of the present subject matter. In an example, the computer-readable instructions for the controller 110 may be processor-executable instructions stored in the memory 108, such as a non-transitory computer-readable storage medium, and the hardware for the controller 110 may include the processing module 112 (e.g., processor(s)), to execute such instructions. In the present examples, the non-transitory computer-readable storage medium stores instructions that, when executed by the processing module 112, implements the controller 110. In an example, the non-transitory computer-readable storage medium storing the instructions may reside outside the system 100, but accessible to the system 100 and the processing module 112 of the system 100. In an example implementation, the controller 110 may be implemented by an electronic circuitry.

The processing module 112 of the system 100 may be implemented as microprocessors, microcomputers, microcontrollers, digital signal processors, central processing units, state machines, logic circuitries, and/or any devices that manipulate signals based on operational instructions. Among other capabilities, the processing module 112 may fetch and execute computer-readable instructions stored in the memory 108, such as non-transitory computer-readable storage medium coupled to the processing resource of the system 100. The non-transitory computer-readable storage medium may include, for example, volatile memory (e.g., RAM), and/or non-volatile memory (e.g., EPROM, flash memory, NVRAM, memristor, etc.).

Further, as shown in FIG. 1, the system 100 includes data 114. The data 114, amongst other things, serves as a repository for storing data that may be fetched, processed, received, or generated by the processing module 112. The data 114 includes parameters settings, such as physiological signal being recorded so as to get detected (and facilitate robotic exoskeleton unit and brain stimulation unit), speed and range of movement of the limb of the patient set by the user interface 116 and to be executed by the robotic exoskeleton unit 104. The data 114 further includes the information related to the first pre-specified time frame and the second pre-specified time frame.

The description hereinafter describes an example procedure of rehabilitating a limb of a patient. The limb that is to be rehabilitated could be an upper limb or a lower limb of the patient. In an example, the limb to be rehabilitated is the upper limb. In an example is the upper limb is a wrist of a hand. The activity related to the movement of the wrist is utilized for performing rehabilitation.

The user interface 116 is coupled to the controller 110 and sets the starting parameters, such as amount of physiological signal patient is able to generate, speed of movement, an initial degree of the range of movement and a final degree of the range of movement of the limb of the patient (according to the individual patient clinical symptoms). The data 114 stores the information related to the speed of movement, the initial degree of range of motion and the final degree of range of motion of the limb of the patient. A motor of the robotic exoskeleton unit 104, through a position feedback on gears connected to a motor shaft of the motor, reaches a baseline position, and then the patient is instructed to make a voluntary attempt in the form of an effort to move the limb for a first pre-specified time frame. In an example, the first prescribed time frame is 3 seconds. The activity monitor 102 monitors the activity or movement of the limb and generates the effort signals related to the movement of the limb of the patient in a first pre-specified time frame. In an example, the activity monitor 102 is a muscle activity monitor. In another example, the activity monitor is a brain activity monitor. In yet another example, the activity monitor 102 is an electro-encephalogram bio-sensor device. In further another example, the activity monitor 102 is an any other bio-sensor device. The first prespecified time frame expires when the effort signal reaches a pre-specified threshold. For the duration of first pre-specified time, the activity monitor regularly detects the activity of the patient in milliseconds to check if the threshold has been crossed. If the threshold has not been crossed, for example, if patient did not put effort/enough effort to try for the movement, it again gives the patient the first pre-scribed time to again try for the effort and it repeats until any of the threshold is crossed. Patient crosses threshold means he tried to put effort for movement and crossed the threshold enough to get the muscles in active state.

Upon the expiry of the first pre-specified time frame, a effort signal is communicated to the controller 110 over a second pre-specified time frame and feedback signal is communicated to patient at the start/during the second pre-specified time. The feedback signal is an output signal and is an outcome of the effort signal. The effort signal is an input signal. The controller 110 receives the effort signal from activity monitor and communicates to the feedback engine to give audio-visual feedback signal to patient over the duration of second pre-specified time. In an example, the second prescribed time frame is 7 seconds. The feedback signal is communicated by the controller 110 and to the feedback engine and finally patient in the form of an audio-visual feedback. The user interface 116 displays the audio-visual feedback. The controller 110 is communicatively coupled to the activity monitor 102 and operatively coupled to the robotic exoskeleton unit 104 and the brain stimulation unit 106. Example of an audio feedback includes a human voice of remarks about the performance. Example of a visual feedback includes number of LED lights in a dot matrix display, scores written in LED lights of dot matrix display, LCD display (with remarks like Good, fair, bad about the performance).

The controller 110, upon the expiry of the first pre-specified time frame and start of the second pre-specified time frame, simultaneously activates the robotic exoskeleton unit 104 and the brain stimulation unit 106 within milliseconds over the initiation of a second pre-specified time frame. The robotic exoskeleton unit 104 completes the movement of the limb of the patient according to a pre-defined set of parameters by the user over the second prespecified time frame. The brain stimulation unit 106 externally stimulates a local motor region of a brain of the patient, based on the effort signal reaching a pre-specified threshold, to complete a sensorimotor loop by movement completion by the robotic exoskeleton unit 104 over the second pre-specified time frame. In an example, the brain stimulation unit 106 is a magnetic brain stimulation unit. In another example, the brain stimulation unit 106 is an electric brain stimulation unit. The local motor region of the brain of the patient controls the movement of the limb of the patient. The system 100 comprises a control circuitry 300 as shown in FIG. 3 to trigger the brain stimulation unit 106 to synchronize a neural activity of the brain generated by the voluntarily attempt of the patient with a brain stimulation, within milliseconds of detecting any physiological signal crossing threshold by the activity monitor 102, over initiation of the second pre-specified time frame, and wherein the neural activity is generated by the voluntary attempt of the patient. The control circuitry is capable of stimulating the brain of the patient depending on the state or activity level of the brain within a set period of time.

The controller 110 activates the brain stimulation unit 106 to perform a single/repetitive pulse brain stimulation on a contralateral hemisphere of the brain that results in the motor evoked potential generation for the limb of the patient. The controller 110 activates the robotic exoskeleton unit 104 to trigger the limb movement simultaneously with the ongoing process of the single/repetitive pulse brain stimulation. The movement completion by the limb provides proprioceptive feedback to a sensorimotor cortex of the brain to create a closed feedback brain stimulation loop. In an example, the brain stimulation is non-invasive. In another example, the brain stimulation is invasive. The feedback unit 118 displays the feedback, in the full duration of second pre-specified time, of the effort signal according to the effort made by the patient and the amount of the effort signal detected. The feedback displayed by the feedback unit 118 enables the patient to have the knowledge about his effort in each cycle.

Figure 2:
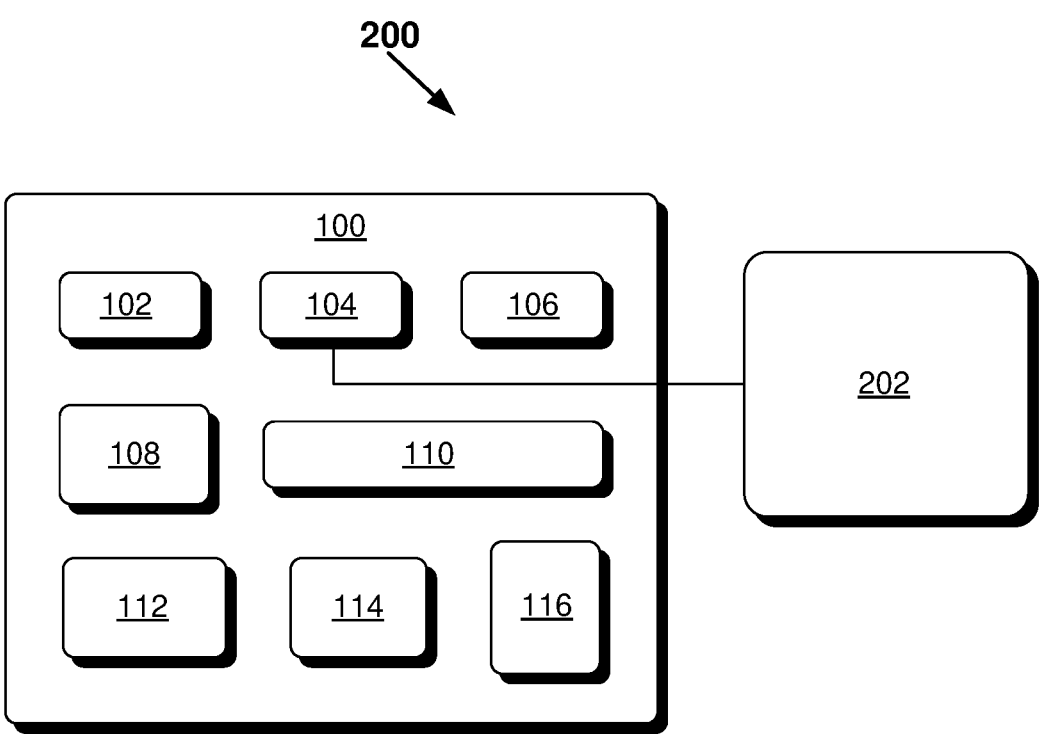
FIG. 2 illustrates a system environment, in accordance with an example implementation of the present subject matter.
Figure 3:
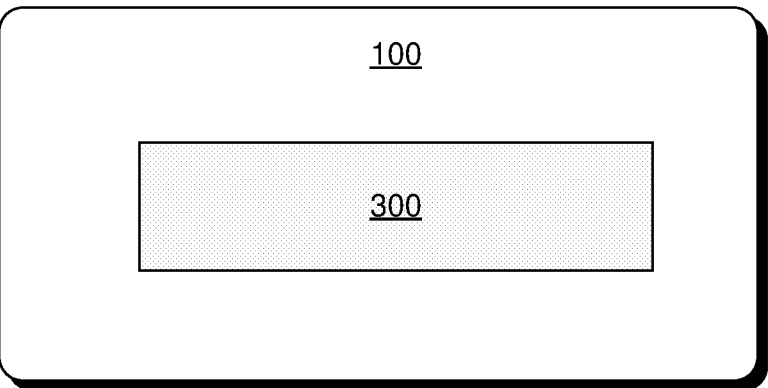
FIG. 3 illustrates a schematic view of a system for rehabilitation of a limb of a patient with a control circuitry, in accordance with an example implementation of the present subject matter.

FIG. 2 illustrates a system environment 200, in accordance with an example implementation of the present subject matter. The system environment 200 includes a system 100 for rehabilitation of a limb of a patient. The system 100 for rehabilitation of a limb of a patient, in addition to an activity monitor 102, a robotic exoskeleton unit 104, a brain stimulation unit 106, a memory 108, a processing module 112, data 114 and a user interface 116, includes a controller 110 that is operably coupled to a feedback engine 202.

The controller 110 receives an input from the activity monitor 102 regarding a performance of the patient, wherein a minor voluntary attempt made by a severely disabled patient is also detected. Based on the input, the controller 110 determines if a cycle period including the first prespecified time frame and the second prespecified time frame can be modified. The controller 110 automatically modifies the cycle period according to the performance of the patient after determining if the cycle period including the first prespecified time frame and the second prespecified time frame can be modified. In an example, the cycle period including the first prespecified time frame and the second prespecified time frame is 10 seconds. In another example, the cycle period including the first prespecified time frame and the second prespecified time frame is 20 seconds. In yet another example, the cycle period including the first prespecified time frame and the second prespecified time frame is 30 seconds.

The cycle period can be adjusted according to the treatment planning of the patients. For evidencing improvement, the patient is instructed to participate for a minimum of 45 minutes a day for four weeks.

Although examples for the present disclosure have been described in language specific to structural features and/or methods, it is to be understood that the appended claims are not limited to the specific features or methods described herein. Rather, the specific features and methods are disclosed and explained as examples of the present disclosure.

We claim:
1. A system (100) for rehabilitation of a limb of a patient, the system (100) comprising:
    an activity monitor (102);
    a robotic exoskeleton unit (104) to assist a movement of the limb of the patient;
    a brain stimulation unit (106);
    a controller (110) communicatively coupled to the activity monitor (102) and operatively coupled to the robotic exoskeleton unit (104) and the brain stimulation unit (106), and
    a control circuitry,
    wherein the activity monitor (102) is to:
        in a first pre-specified time frame, detects an activity of the limb of the patient by a voluntary attempt of the patient and generate an effort signal based on the detection; and
        upon expiry of the first pre-specified time frame, communicate the effort signal to the controller (110) over a second pre-specified time frame, wherein the controller (110) is to, upon expiry of the first pre-specified time frame, simultaneously activate the robotic exoskeleton unit (104) and the brain stimulation unit (106) over the initiation of second pre-specified time frame, wherein the robotic exoskeleton unit (104) is to complete the movement of the limb of the patient, according to pre-defined set of parameters by the user, over the second pre-specified time frame, wherein the brain stimulation unit (106) is to externally stimulate a local motor region of a brain of the patient to complete a sensorimotor loop over the second pre-specified time frame, wherein the local motor region of the brain of the patient controls the movement of the limb of the patient, wherein the control circuitry is to trigger the brain stimulation unit (106) to synchronize a neural activity of the brain generated by the voluntarily attempt of the patient with a brain stimulation, within milliseconds of detecting by the activity monitor (102), over initiation of the second pre-specified time frame, the neural activity being generated by the voluntary attempt of the patient, and wherein the activity monitor (102) comprises a feedback engine (202) coupled to the controller (110), wherein the controller (110) is to;

receive an input from the activity monitor (102) on the basis of which the effort signal is given as a performance of the patient based on the signal effort;

based on the input, determine if a cycle period including the first prespecified time frame and the second pre-specified time frame can be modified; and based on the determining, automatically modify the cycle period according to the performance of the patient.

2. The system (100) as claimed in claim 1, wherein the first pre-specified time frame expires, when the effort signal reaches a pre-specified threshold.

3. The system (100) as claimed in claim 1, wherein the effort signal is communicated to the controller (110) over full second pre-specified time frame in the form of an audio/visual feedback.

4. The system (100) as claimed in claim 3, wherein the system (100) comprises a user interface (116), coupled with the controller (110) to:

assist the patient to set a predetermined set of parameters for enabling the movement of the limb; and provide the audio-visual feedback over the second pre-specified time frame.

5. The system (100) as claimed in claim 4, wherein the user interface (116) is integrated with the controller.

6. The system (100) as claimed in claim 1, wherein the activity monitor (102) is a biosensor.

7. The system (100) as claimed in claim 1, wherein the activity monitor (102) is a muscle activity monitor.

8. The system (100) as claimed in claim 1, wherein the brain stimulation unit (106) is a magnetic unit.

9. The system (100) as claimed in claim 1, wherein the brain stimulation unit (106) is an electric unit.

* * * * *